United States Patent [19]

North, Jr.

[11] Patent Number: 5,040,890

[45] Date of Patent: Aug. 20, 1991

[54] SHEATHED PARTICLE FLOW CONTROLLED BY DIFFERENTIAL PRESSURE

[75] Inventor: Howard L. North, Jr., Los Gatos, Calif.

[73] Assignee: Becton, Dickinson and Company, Franklin Lakes, N.J.

[21] Appl. No.: 125,095

[22] Filed: Nov. 25, 1987

[51] Int. Cl.$^5$ ............................................. G01N 21/01
[52] U.S. Cl. ............................................. 356/72; 356/73
[58] Field of Search ............ 356/72, 73; 73/199, 73/861.42, 861.44; 324/71.4, 71.1; 209/552

[56] References Cited

U.S. PATENT DOCUMENTS

| | | | |
|---|---|---|---|
| 4,070,617 | 1/1978 | Kachel et al. | 324/71.1 |
| 4,285,245 | 8/1981 | Kennedy | 73/199 |
| 4,503,385 | 3/1985 | Haynes | 324/71.4 |
| 4,683,212 | 7/1987 | Uffenheimer | 356/73 |

Primary Examiner—Richard A. Rosenberger
Attorney, Agent, or Firm—Aaron Passman

[57] ABSTRACT

A flow apparatus for the analysis of particles passing substantially one at a time through an analysis region includes a flow rate control responsive to changes in the pressure used to drive the particles through the analysis region. The flow rate control automatically regulates the flow to a preset value throughout the analysis by adjusting the particle driving pressure to be uniform even though the sheathe liquid supply is depleted during the analysis. A method for controlling the flow of a supply of particles to be analyzed includes steps of sensing differential pressure and regulating the differential pressure to a preset reference.

12 Claims, 4 Drawing Sheets

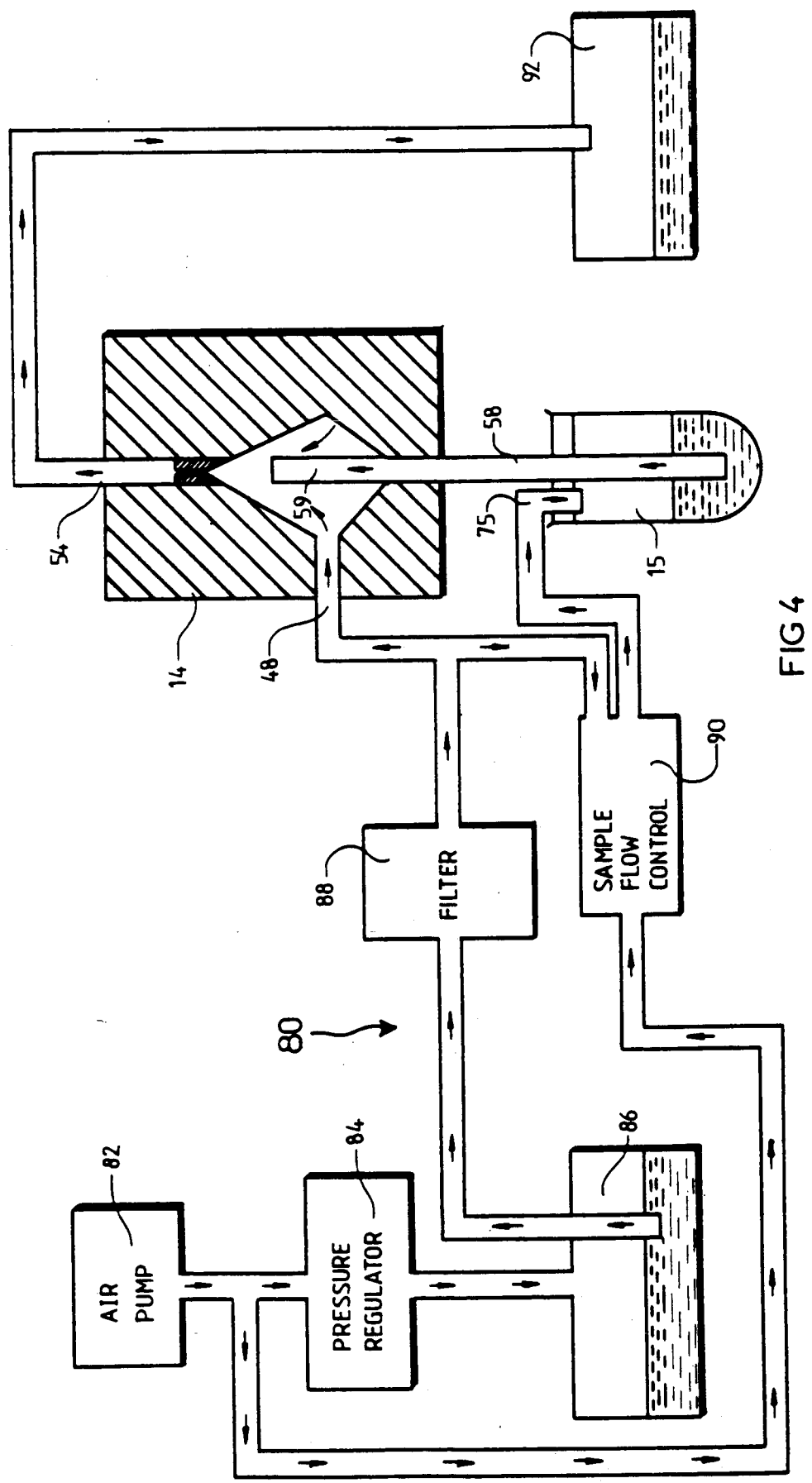

SHEATHED PARTICLE FLOW CONTROLLED BY DIFFERENTIAL PRESSURE

BACKGROUND OF THE INVENTION

1. Field of the Invention

The present invention relates to an automatic differential pressure control for a particle flowthough apparatus which includes an electronic pressure monitoring feature, and more particularly, concerns a flow cytometer for determining one or more characteristics of particles flowing in a flow cytometer with such an automatic pressure control wherein the flow rate of ensheathed particles can be regulated and maintained at a preset level to facilitate the uniform operation of the apparatus. The method of using a technique to automatically control particle flow is also a part of the present invention.

2. Description of the Prior Art

There are a number of cell or particle analyzing devices using flow cytometer equipment and techniques which rely on hydrodynamically focused fluid flow through an analysis orifice where the specific characteristics of the flowing cells or particles can be determined. Flow analysis of particles has been used in the determination of the variety of characteristics of individual particles. This analysis is most useful in determining characteristics of cells for the collection of information which would aid in areas of research, hematology, immunology and the like. The researcher, for example, could be interested in determining specific characteristics of the individual cells where those cells need to be classified, identified, quantified and perhaps sorted for further investigations or analysis.

One commercially available flow cytometer which relies on a hydrodynamically focused fluid system is known as the FACScan TM instrument sold by the Becton Dickinson Immunocytometry Systems, Mt. View, Calif. The FACScan instrument rapidly analyzes cells on the basis of fluorescence and light scatter properties. Analysis is accomplished by introducing cells in suspension to the center of a focused liquid stream and causing them to pass, one at a time, through a focused light from a high power lamp or laser. Each cell is individually characterized by its light scatter signals and by the intensity and color of fluorescence emitted while it is illuminated.

In the aforementioned flow cytometer, a sheath liquid focuses the particles or cells as they pass through the orifice associated with the analyzing or counting capabilities. U.S. Pat. Nos. 4,503,385 and 4,526,276 describe particle analysis systems in which particles flowing in a stream are enveloped in a sheath liquid which focuses and confines the sample liquid (with the particles or cells) to the center of the flowing stream. U.S. Pat. No. 4,110,604 describes a particle density measuring system in which particles flowing in a stream are enveloped in a sheath liquid which focuses and confines the sample fluid (with the particles) to the center of the flowing stream.

Early systems provided for independent regulation of the air pressure used to drive the liquid with sample particles or cells from a supply test tube and of the air pressure in the sheathing liquid supply reservoir. The independent manual regulation and separate control of these two air pressures did not overcome the errors and disturbances produced by changes in liquid level in the sheathing liquid supply reservoir and pressure drop at the sheath liquid filter as it became partially obstructed with contamination or air. The air pressure regulator for the sheathing liquid supply and the other regulator for the sample test tube are required to be manually controlled. However, if reservoirs are depleted the air pressure generating the flow must be increased to maintain the proper flow rate. If the air pressure does not maintain the particle flow through the analysis orifice, the operation of the cytometer is impaired.

In the presently known and available particle flow-through equipment, electrically operated pumps, syringe pumps or the like are used in the fluidics of the system to move the liquid and particle flow through the flowcell analysis orifice and passageways. The Assignee of the present application has a co-pending application, U.S. Ser. No. 866,003 filed May 22, 1986, disclosing a housing for a flow cytometer apparatus with a particle unclogging feature The usual operation for these pumps is to force or draw liquid with particles from a sample test tube through a sample capillary tub centered in the sheathing liquid flowing in the direction of the particle analysis orifice. These syringe pumps used to aspirate and supply the sample to the analysis orifice tend to produce carryover, washout and other problems.

With the foregoing in mind, improved techniques for overcoming pressure differential variation in particle flow-through equipment are still being sought. Such improvements in a particle flow control should preferably be included in the particle flow-through apparatus so that the various parts thereof do not have to be constantly adjusted as the sheathing liquid reservoir is depleted. It is toward such an improvement that the present invention is directed.

SUMMARY OF THE INVENTION

The automatic differential pressure control automatically regulates and maintains the air pressure used to drive the sample liquid with particles from the test tube and can also, if needed, regulate the air pressure used to force the sheathing liquid from its reservoir. By controlling the differential pressure between the test tube and sheathing liquid pressures, uniform particle flow rates are achieved. The air pressure for driving liquid with sample particles through a capillary tube is sensed at a pressurizing air inlet for the sample test tube. A sheathing liquid pressure is also monitored at the inlet to the flow analysis apparatus. A differential pressure transducer is connected across the aforesaid inlets of the particle flow-through apparatus of the present invention.

The apparatus has a housing with a body member having a passageway therethrough including an analysis region through which substantially one particle at a time passes in the direction of flow during operation. The differential pressure transducer provides a signal to regulate the pressure in the sample test tube for overcoming changes due to depletion of supply and to filter clogging. The object is to maintain a preset particle flow rate through the analysis orifice.

In a preferred embodiment of this aspect of the invention, the housing is suitable for a flow cytometer and includes a body member having a passageway therethrough for the passage of particles or cells which are to be analyzed. The passageway includes a pre-analysis portion, an analysis portion and a post-analysis portion aligned in that order along the axis of the passageway in that direction of flow. An air pressure supply is used for the sample test tube and another for the sheathing liquid reservoir. A differential pressure transducer is in fluid communication with the sheathing liquid inlet to the pre-analysis portion of the passageway and is also in fluid communication with the inlet of the pressurizing air for the sample test tube. The differential pressure transducer provides a varying electrical signal proportional to the monitored pressure differences. A comparator, which receives that signal and a preset reference, provides an operative control output relative to the difference therebetween. A regulator connected to receive that control output maintains the pressure differential at a preset level even though the transduced pressures vary independently of one another. The variation in transduced particle flow differential pressure is more important to the proper operation of the apparatus and is, therefore, the regulated preferred parameter.

In another aspect of the present invention, a flow cytometer is used for determining one or more characteristics of particles or the like flowing in a liquid stream. A body member has a passageway therethrough including an analysis region through which the moving particles pass substantially one at a time in the direction of flow. Differential pressure transducer means is provided to monitor the pressure difference between the pressure for moving particles and the pressure for moving the sheathing liquid flow stream. Changes in differential pressure are automatically regulated to a preset difference. Means is included for providing a beam of light to illuminate the particles passing through the analysis region. Means detects light with respect to each moving particle and associates the detected light with one or more characteristics of each particle.

In accordance with the principles of the present invention, an automatic, electronic circuit with a transducer, a comparator, and a controller are preferably associated with a housing for inclusion in a particle flow through apparatus such as a flow cytometer. The automatically operating electronic circuit regulates the sample test tube air pressure used to transport particles into the passageway, including the capillary tube and the analysis orifice within the housing. The preferred embodiment provides compensation for the pressure drop due to the change in the reservoir liquid level during the operation of the cytometer.

This automatically operated control may also operate an air pump and/or regulators to supply required pressures which are necessary when debris clogs the filter. The feature of the present invention for accommodating varying liquid levels is easy to construct, simple to operate and primarily and directly regulates pressures applied to the sample test tube head space for controlling particle flow rate of a particle flow-through apparatus. By including the aforementioned monitoring and regulating features in the housing for a particle flow-through apparatus, the automatic system performs uniformly throughout cytometric study without manual readjustment.

The method for controlling the flow rate through a particle analysis apparatus includes transporting a sample of particles carried in a liquid by regulating air pressure applied to the liquid. The method further includes sensing the pressure difference between the air driving the sample and pressure of the liquid which ensheathes the sample. Thereafter, the method requires developing an electrical signal relative to the pressure difference sensed. An electrical reference signal of a pre-selected value relative to the desired sample flow rate is then provided. The electrical reference signal and the pressure difference signal are compared to generate an error signal. The error signal is then used to operate a pressure regulator.

Other advantages of the present invention will be perceived and understood by reading the detailed description which follows below.

BRIEF DESCRIPTION OF THE DRAWINGS

FIG. 4 is a schematic illustration of the relationship of the pressure control flow paths and the sample flow control including the connections of the control with the analyzer of FIG. 1.

DETAILED DESCRIPTION

Figure 1:
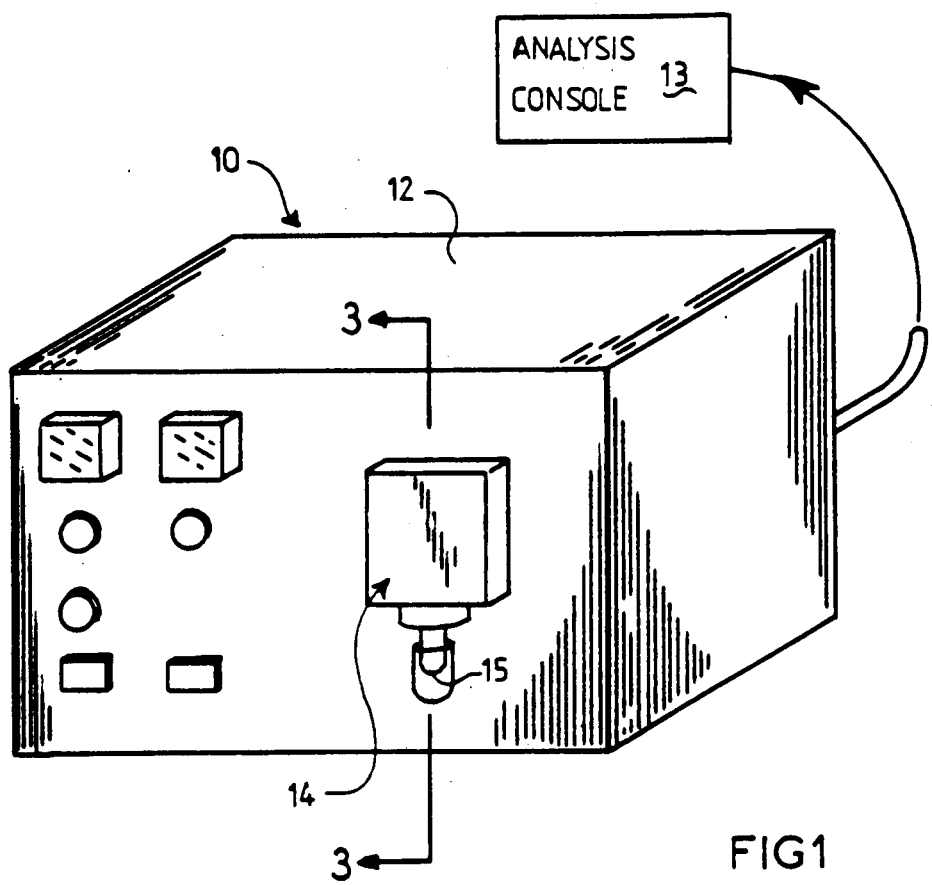
FIG. 1 is a perspective view of the preferred embodiment of a flow cytometer with an automatic flow control for use in determining one or more characteristics of particles or the like flowing in a liquid stream.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Referring to the drawings, and FIG. 1 in particular, there is illustrated a flow cytometry apparatus 10 of the present invention for determining one or more characteristics of particles or the like. Apparatus 10, for example, may be a cell analyzer which includes a liquid sampling console 12 which is constructed to contain particle or cell detection and analysis elements as hereinafter described. In particular, apparatus 10 includes a liquid sampling console 12 which is constructed to contain the particle, light scatter and fluorescence measuring components, as hereinafter described, but which is separate from the analysis console 13. It will be pointed out hereinafter that analysis console 13 includes the electrical components, display screens and other data information regarding the control and function of the apparatus 10. Liquid sampling console 12, as seen in FIG. 1, includes a flow manifold assembly in the form of a housing 14 which is designed to provide a stream of flowing liquid containing the particle to be analyzed. In the apparatus being described, the particles for analysis may be included in a test tube 15 which can be removably positioned onto housing 14. Before describing the details of housing 14, a general description of the optical and flow elements of flow cytometry apparatus 10 will be provided.

Figure 2:
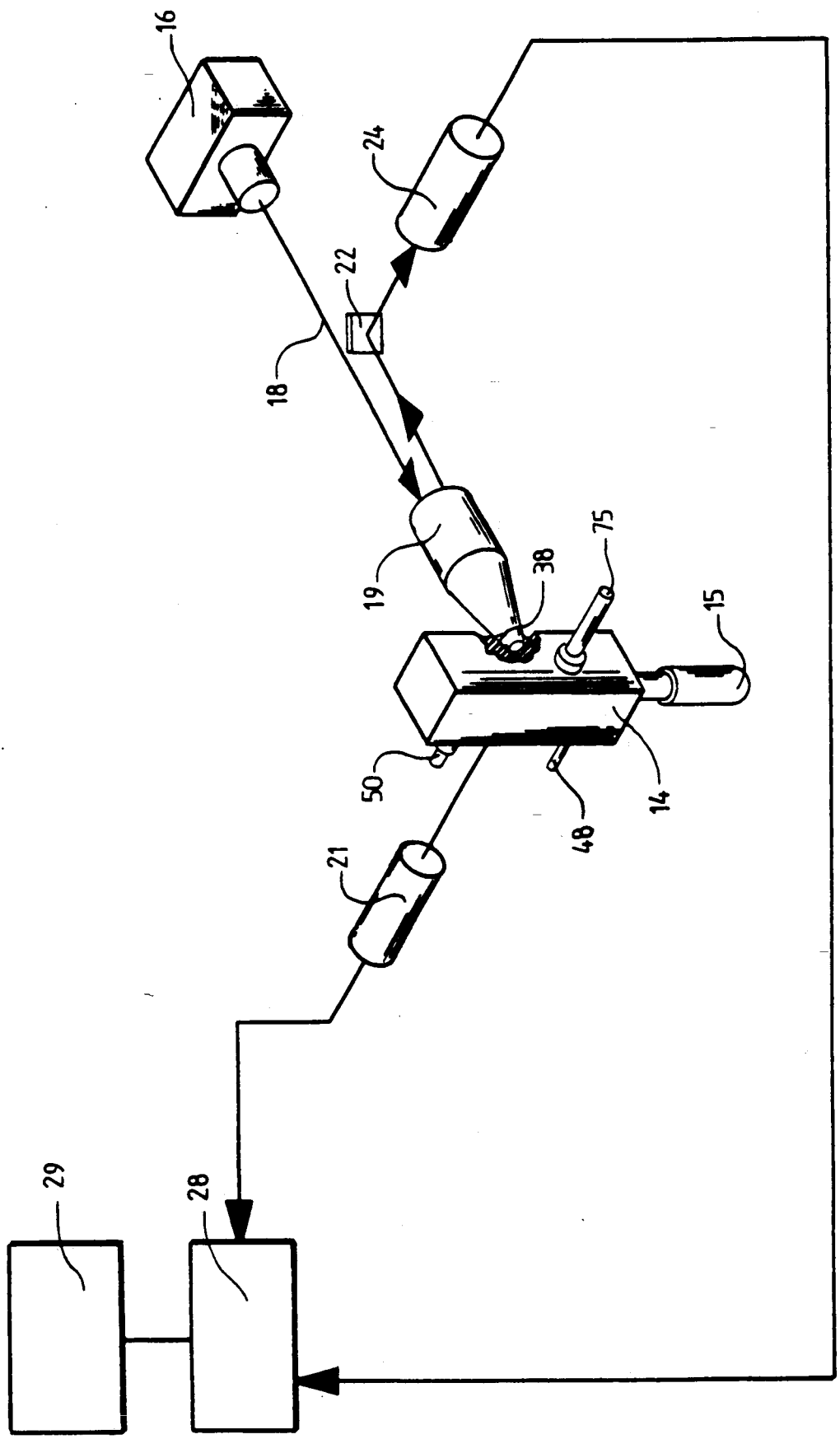
FIG. 2 is a schematic illustration of typical elements and light paths of a flow cytometer embodying the sample flow control of the present invention.

FIG. 2 is a schematic illustration of the general optical and flow elements embodied in the preferred flow cytometer of the present invention. In addition to the general optical and flow elements of the apparatus to be described, other details of a cell analyzer apparatus useful in conjunction with the present invention are described in European Patent No. 0068404. It is understood that the housing 14 of the present invention is useful in many different types of flow cytometry or flow fluorometric equipment which measure light scatter, fluorescence, or other optical parameters for the identification, quantification or enumeration of cells, particles or the like in a sample liquid medium. As illustrated in FIG. 2, light energy is provided for the flow cytometer by a light source 16 such as a laser which provides a coherent beam of light at a singular wavelength or an arc lamp, such as a mercury or xenon arc lamp, which provides an incoherent beam of light comprising a broad spectrum of wavelengths.

Excitation energy is transmitted in the flow cytometer by a beam of light 18 produced by light source 16. Typically, the beam of light passes through focusing lens 19 which focuses the light beam at the liquid stream containing the particles or cells under investigation, and which will be described in more detail.

As each cell or particle passes through the focused light region where light beam 18 intersects the flowing liquid stream, light scattered by the cell or particle can be detected by an appropriate photodetector 21. Similarly, fluorescence, if emitted by particles energized by the illumination from the light source, can also be detected. Fluorescence emitted by autofluorescent particles or fluorescently labeled or stained particles in the liquid stream can be detected along the same axis as light beam 18 through lens 19, which, may, for example, be a condenser lens assembly. This lens assembly is preferably, but not necessarily, an epi-illuminating system which uses the same lens for imaging excitation light and for receiving fluorescence emission from the particles.

Fluorescence emitted by the flowing particles can be directed to a dichroic mirror 22 before being collected by fluorescence detector 24. More than one fluorescence detector may be employed in order to detect fluorescence emitted from the particles at different wavelengths. Photodetector 21 and fluorescence detector 24 are well-known photomultiplier tubes, or similar devices which convert light signals into electrical impulses, so that the light thereby detected may be associated with the fluorescently labeled cells and cells of a specific size flowing through the apparatus. The electrical signals from photodetector 21 and fluorescence detector 24 are typically fed to the electronics 28 of the apparatus for purposes of display 29, storage or further processing so that one or more characteristics of the cells or particles under analysis can be determined. Electronics 28 may be included in an analysis console 13, if desired.

Figure 3:
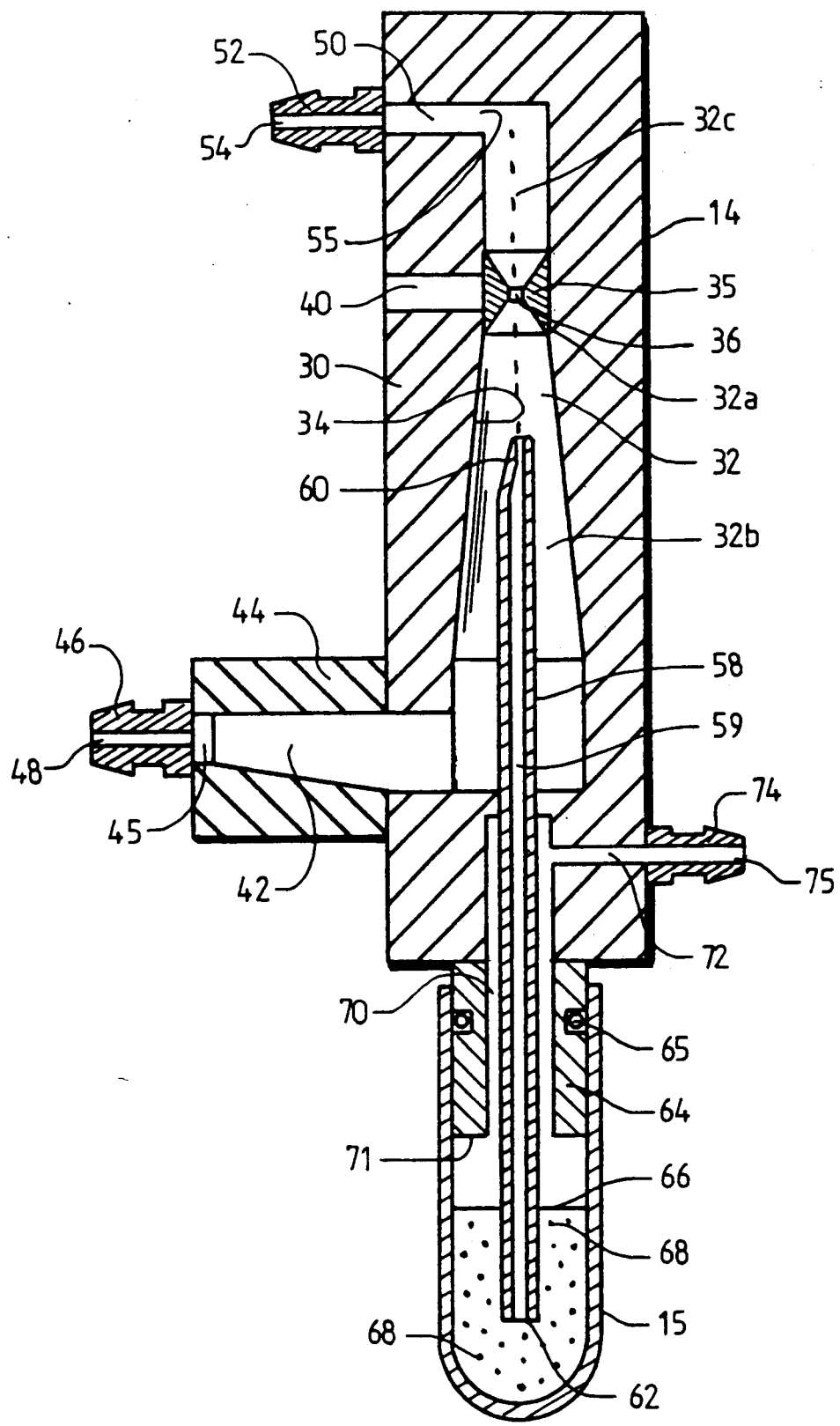
FIG. 3 is a enlarged cross-sectional view of the preferred flow housing of the present invention taken along line 3—3 of FIG. 1.

Turning now to FIG. 3, the details of housing 14 of the present invention are more clearly illustrated. It can be seen that housing 14 includes a body member 30 which, in the embodiment being described, is preferably in the form of a block or rectangular prism. Although not shown in the drawings, the block form of housing 14 facilitates the mounting of the housing within the flow cytometer apparatus 10. Extending through housing 14 is a passageway 32 which is defined by three segments: an analysis portion 32a, a preanalysis portion 32b, and a post-analysis portion 32c. As seen in FIG. 3, the pre-analysis, analysis and post-analysis portions of passageway 32 lie on the same axis through body member 30 and are arranged in that order relative to the direction of particle flow through the passageway 32.

It is preferred that analysis portion 32a and post-analysis portion 32c of the passageway be cylindrically shaped bores extending into body member 30. On the other hand, it is preferred that pre-analysis portion 32b of the passageway be tapered so that it includes tapered walls 34 defining a frustoconical passageway having its narrow end facing toward analysis portion 32a of the passageway.

Preferably positioned within analysis portion 32a of the passageway is a flowcell or flow chamber 35 which facilitates the analysis of cells or particles under investigation. Flowcell 35 includes an orifice 36 which is preferably sized to permit the passage of substantially one particle at a time therethrough. As a light beam intersects the region defined by orifice 36, particles or cells which pass through the orifice also pass through the light beam thereby establishing a basis for a light-related signal which can be detected.

So that light energy can be available to illuminate the region defined by orifice 36 in the flowcell, body member 30 of the housing includes a recess 38 into which lens assembly 19 is positioned so that the lens assembly lies adjacent flowcell 35. This type of arrangement suggested by the illustration in FIG. 2 is consistent with a technique known as epi-illumination for providing light energy to interrogate the particles under analysis. Light is directed through lens assembly 19 at an angle substantially orthogonal or at a right angle, to the aforementioned direction of particle flow through the flowcell. Lens assembly 19 can include one or more lenses in a condenser lens assembly for focusing incident light on the particles which pass through orifice 36, and may receive light such as fluorescence from the particles which have been illuminated by the incident light beam 18. Of course, the present invention contemplates that light from the particles may be detected in any direction with respect to the axis of the incident light beam.

The appropriate light detectors are positioned at the desired angle for collecting light scattered or emitted by the particles or for detecting light energy absorbed by the particles. To this end, as seen in FIG. 3 one or more windows 40 extend through body member 30 into flowcell 35 through which light passes for collection by the photodetector elements. On the other hand, it is not necessary to provide such a window if body member 30 is sufficiently light transmissive to allow light to pass therethrough in sufficient strength to be detected. It is, however, preferred that flowcell 35 be light transmissive and also that the flowcell be removable from body member 30 in the event that it needs cleaning, replacement or change.

Body member 30 also includes a first channel 42 which is in fluid communication with pre-analysis analysis portion 32b of the passageway. Channel 42, in this embodiment, extends through a side block 44 of body member 30 so that this channel is substantially at right angles to the axis of passageway 32. Side block 44 includes a valve 45, or like device, which is operative to selectively open or close channel 42. Although not shown in FIG. 3, valve 45 can be operated manually, electrically, pneumatically or any other convenient technique of operation. A fluid connector 46 is positioned on side block 44 so that its lumen 48 is in fluid communication with channel 42. It is the purpose of channel 42 to provide a passageway for the introduction of a liquid for sheathing particles which flow into analysis portion 32a of the passageway, and which more specifically flow through flowcell 35. The provision of a sheath liquid for a hydrodynamically focused fluid flow system is well-known in the art and is described in the mentioned patents. The sheath liquid is generally pressured with air and typically flows through channel 42 at a pressure of between 0.5 and 10 psi and at a rate of 10 to 20 ml. per minute. The sheath liquid is usually a saline solution which is substantially particle free so that it does not interfere with the analysis.

Communicating with post-analysis portion 32c of the passageway is another channel 50 which also extends through body member 30 in the embodiment being described. Second channel 50 also preferably extends at substantially right angles to the axis of passageway 32. In fluid communication with channel 50 is a fluid connector 52 having a lumen 54 therethrough. It is the purpose of channel 50 to provide a passageway for the passage of particles and liquids out of housing 14 after passing through the analysis portion of the passageway. It can be seen that channel 50 has its interior end 55 preferably open to post-analysis portion 32c of the passageway.

Particles or cells to be analyzed are preferably transported through a hollow tube 58 with a lumen 59 extending therethrough. Tube 58 extends substantially along the axis of passageway 32 and has an inner end 60 positioned in pre-analysis portion 32b of the passageway. It is preferred that inner end 60 be positioned within tapered walls 34 of the pre-analysis portion so that the inner end 60 of the tube lies adjacent flowcell 35 in the analysis portion of the passageway. Tube 58 has its outer end 62 extending outwardly of body member 30. The body member of the housing preferably includes a circularly shaped extension 64 through which tube 58 extends before passing outwardly of the body member. A gasket 65, or other like element for providing a liquid-tight seal, is positioned around circularly shaped extension 64. It can be seen in FIG. 3 that test tube 15 is positioned so that it fits onto extension 64 with gasket 65 facilitating a liquid-tight seal between the test tube and extension 64 of the body member. Test tube 15 includes sampling liquid 66 and particles 68 to be analyzed. Outer end 62 of the tube extends into sampling liquid 66 in this embodiment.

In order to cause particles 68 in the sampling liquid to be transported into tube 58, an annular passageway 70 is provided around the exterior surface of tube 58. This annular passageway includes an open end 71 surrounding tube 58 at the distal end of extension 64. A third channel 72 extends through body member 30 and is in fluid communication with annular passageway 70. A fluid connector 74 on the side of the body member includes a lumen 75 which is in fluid communication with channel 72. It is the purpose of connector 74 to be connected to a source of regulated pressurized air or other fluid to serve as a driving force of pressure into the test tube so that sampling liquid 66 and particles 68 may pass through lumen 59 of tube 58. Normally, the air is delivered through channel 72 at a slightly higher pressure than that applied to drive the sheath liquid through channel 42. In the preferred case, the regulated air pressure may be controlled at 5.0 psi or 4.0 psi for a selected high or low flow rate of 1.5 microliters per second, or 0.25 microliters per second, respectively.

Particles 68 pass out of the inner end of the tube into pre-analysis portion 32b of the passageway. Here, the particles and sampling liquid become ensheathed by the sheathing liquid so that the particles pass substantially one at a time through orifice 36 in flowcell 35, as seen in FIG. 3. The confluence between the sampling liquid (and particles) and the sheath liquid form a coaxial, bi-component stream. The sampling liquid containing the particles 68 to be analyzed forms the inner component of the flowing stream. When the stream enters the flowcell 35, there is substantial equilibration in the velocities of the sheath liquid and the sample liquid and the particles are hydrodynamically focused of centered in the middle of the stream away from the walls of the flowcell.

Once in the flowcell, the particles are interrogated by light which enters the flowcell through lens assembly 19 so that light-related information may be determined with respect to each particle. After the particles, sampling liquid and sheathing liquid pass through the analysis region of the passageway, flow continues through channel 50 for passage out of housing 14.

It is appreciated that the various air pressures and resulting flow rates could be manually adjusted by controls on the liquid sampling console. A typical sample flow rate is in the range of 0.25 to 1.5 microliters per second of sampling liquid through the sampling tube. Furthermore, the air pressure in channel 72 may be adjusted to control the count rate of particles through the flow chamber. Typically, the count rate would range between 100 and 1,000 particles per second flowing through the flow cell 35. The design of passageway 32 and the positioning of sample tube 58 therein is intended to offer minimal flow resistance to the bi-component stream of liquid as it flows toward flowcell 35.

In FIG. 4 there is a schematic illustration of the air pressure control 80 for the sample test tube 15, whereby the flow rate of particles 68 is regulated. The air pressure control 80 includes an air pump 82 connected to a pressure regulator 84 adjusted to provide a head pressure input of about 4.5 psi to the sheath liquid supply reservoir 86. The outlet from reservoir 86 is preferably connected to a filter 88 which removes any particulate matter from the sheath liquid as it is transported to the lumen 48 of side block 44. During use, the drop in sheath liquid level and pressure drop across filter 88 are not significant with regard to the flow rate of sheathing liquid at the pre-analysis portion 32b of passageway 32. The change in head pressure in reservoir 86 has been found to be less than 0.2 psi as the liquid level in the reservoir 86 drops from full toward empty.

Air pump 82, in FIG. 4, is also connected to the sample flow control 90 for providing pressurized air to be used to drive the liquid 66 and particles 68 through tube 58 into pre-analysis portion 32b of housing 14. Sample flow control 90 regulates the air pressure applied to test tube 15 through lumen 75 so that the pressure is at 4 psi or 5 psi depending upon whether a low or a high flow rate of particles 68 is desired. Without regulation, the pressure in channel 42 can change significantly during a flow analysis as the liquid is driven from reservoir 86. A waste reservoir 92 is connected to lumen 54 to collect the liquids and particles after they have passed through the post-analysis portion 32c of the passageway 32.

Figure 5:
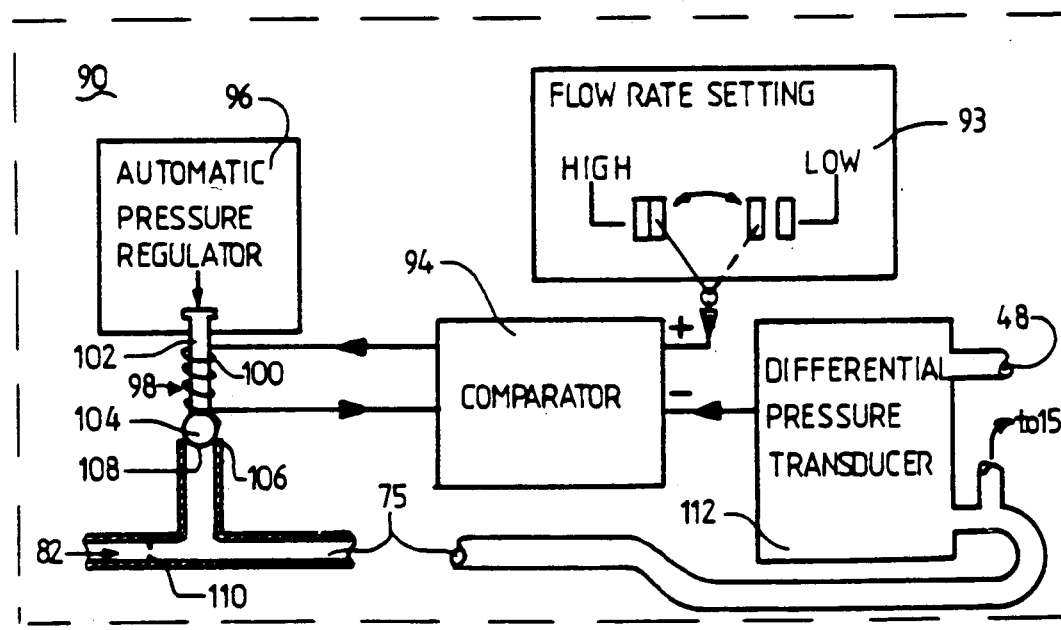
FIG. 5 is a block diagram schematic illustration of the sample flow control used in the analyzer of FIG. 1 to regulate the flow rate of the particles through the analysis portion of the housing.

The sample flow control 90 is shown in schematic block diagram form in FIG. 4; more details are illustrated in the schematic shown in FIG. 5. A sample flow rate setting switch 93 can be preset at a high flow rate setting (for liquid 66 and particles 68) of 1.5 microliters per second, or a low flow rate setting of 0.25 microliters per second as required for the sample to be tested by particle flow analysis. The switch 93 is shown connected to the high flow rate setting; a broken line illustrates the switch connection for the low setting.

The difference in the high and low setting for a switch 93 is a change in preset reference voltages indicated as a positive electrical input signal for a comparator 94. Comparator 94 in the preferred embodiment includes an operational amplifier in an integrator mode circuit whereby accurate control output signals are delivered for use in regulating the air pressure supplied to test tube 15 by way of the lumen 75. As can be seen in FIG. 5, the comparator 94 is connected electrically in circuit with an automatic pressure regulator 96 which is in the nature of an electrically operated valve. Regulator 96 includes a solenoid 98 having an electromagnetic coil 100 and a resiliently biased plunger 102 responsive to currents flowing through coil 100. The coil 100 is connected electrically to the output of the comparator 94 and in a known manner generates an electro-magnetic field responsive to the comparator output. Plunger 102 is normally biased or urged against a valve ball 104 which is held against a valve seat 106 to seal a bleed port 108 located therebeneath.

Air pressure from pump 82 through lumen 75 is regulated by ball 104 to maintain either the high or low particle flow rate setting by bleeding off excess air pressure when the ball 104 is allowed to unseat. In particular, the plunger 102 is drawn away from the ball 104 when the coil 100 is energized allowing air pressure between pump 82 and lumen 75 to decrease to the proper value. An air flow restrictor 110 is located in the air supply between the pump 82 and the valve seat 106, so that air available for bleeding through port 108 does not exceed the capacity of air pump 82. The resilient bias of the plunger 102 is such that the regulator 96 does not become unstable and produces sufficiently high pressures in lumen 75 when coil 100 is not energized. Specifically, undesirable oscillation or sympathetic harmonics of the plunger are avoided by the proper selection of components so that the operation of the valve ball 104 is controlled. The air pressure applied to the test tube 15 via lumen 75 is thus modulated as required to produce the desired differential pressure.

The sample flow control 90 receives an input signal in order to stimulate comparator 94 into generating an appropriate output for activating solenoid 98 of the automatic pressure regulator 96. A differential pressure transducer 112 is used to convert the pressure difference between the sheathing liquid pressure monitored in lumen 48 and the air pressure in sample test tube 15 as measured in lumen 75. The change in liquid pressure in lumen 48 is about 0.2 psi during operation of the apparatus 10 and that decrease is relatively insignificant. Throughout an analysis procedure differential pressure between lumen 48 and lumen 75 is about 1.2 psi when the analyzer apparatus 10 is set for the high particle flow rate and is approximately 0.2 psi when the apparatus 10 is set for the low particle flow rate. It should be appreciated that both the sheath liquid pressure and sample air pressure will decrease, but only the sample air pressure will decrease significantly.

Previous manual independent regulation of the air pressure required constant manual adjustment in order to maintain the preferred particle flow rate through orifice 36. The differential pressure transducer 112, in the preferred embodiment, preferable includes a solid state strain gauge device having a silicon diaphragm with Wheatstone bridge circuitry which produces a changing signal as a functional of strain or load on the diaphragm. In this application, the saline sheathing liquid in lumen 48 pressurizes one side of the diaphragm and the sample air pressure in lumen 75 is against the other side.

As is known, the variations in liquid and air pressures produce a signal which, in the preferred embodiment, is a voltage applied to the negative input of the comparator 94, as shown in FIG. 5. The varying voltage output of differential pressure transducer 112 is directly proportional to the change in the differential air and liquid pressures sensed in lumens 75 and 48, respectively. When the transducer voltage is compared to the (high or low) reference voltage, the resulting output directly controls bleed off of excess air pressure. The capacity of pump 82 is more than adequate to assume that the air pressure in lumen 75 may be maintained at the required level for regulation of particle flow rate. While the liquid pressure in lumen 48 does change somewhat, that change is sensed by the input to transducer 12 and is thus accounted for. The significant air pressure in lumen 75 is directly regulated by sample flow control 80.

What is claimed is:

1. A sample flow control for a flow cytometer comprising:
   a body member having a passageway therethrough for the passage of particles which are to be analyzed, said passageway including an analysis portion, a pre-analysis portion and a post-analysis portion;
   a differential pressure transducer in fluid communication with a sheath liquid supplied to said pre-analysis portion of said passageway and adapted for fluid communication with the test tube containing a sample of particles connected to said pre-analysis portion of said passageway for providing a differential pressure input signal equivalent to the pressure difference therebetween;
   comparator means connected to receive said input signal and a preset reference signal for providing an operative control output comprising the difference between the signals; and
   regulating means powered by said operative control output to maintain the pressure applied to the sample test tube for driving particle flow therefrom at a preestablished flow value.

2. The control of claim 1 wherein the analysis portion of said passageway includes a flowcell having an orifice sized to permit the passage of substantially one particle at a time through said analysis portion, and wherein said regulating means includes an air pump operative to maintain the pressure applied to the sample test tube to drive particles through said orifice at the preestablished flow rate.

3. The control of claim 2 wherein said body member includes means for permitting light to be directed at said orifice at an angle substantially orthogonal to the direction of particle flow through said flowcell.

4. The control of claim 3 wherein said means for permitting light includes a recess for positioning a lens adjacent said flowcell.

5. The control of claim 2 which further includes a sample tube having an inner end positioned in said pre-analysis portion of said passageway and an outer end extending outwardly of said body member into the sample test tube, said sample tube having a lumen extending therethrough for the passage of particles from said test tube toward the analysis portion of the passageway.

6. The control of claim 5 wherein a pressure regulating transducer is connected to receive controlling input from said comparator means operative output for regulating an air supply to pressurize said sample test tube containing particles supplied through said lumen to said passageway pre-analysis portion.

7. The control of claim 6 wherein said preanalysis portion includes a tapered segment which narrows toward said analysis portion, the inner end of said sample tube being positioned within said tapered segment adjacent the analysis portion.

8. The control of claim 7 wherein a sheathing liquid is introduced into said preanalysis portion about said sample tube inner end to provide a sheathed flow of particles along an axis of the passageway toward said analysis portion.

9. A method for controlling the flow rate through a particle analysis apparatus transporting a sample of particles carried in a liquid by regulating air pressure applied to the liquid including the follow steps;

sensing a pressure difference between air driving a sample of particles and liquid to ensheath the sample, developing an electrical signal relative to the pressure difference sensed, providing an electrical reference signal of a preselected value relative to a desired sample flow rate, comparing the electrical reference signal and the pressure difference signal to generate an error signal, using the error signal to operate a pressure regulator, and effecting a control function of the pressure regulator for at least one of the differential pressures sensed.

10. The method of claim 9 wherein the step of effecting control includes an operator used for control to provide stable regulation.

11. The method of claim 9 wherein the step of using includes integrating the error signal in an operational amplifier circuit.

12. The method of claim 9 wherein the step of providing at least two reference signals permits the selection of two or more sample flow rates.

* * * * *